(12) United States Patent
Reed et al.

(10) Patent No.: US 6,676,934 B1
(45) Date of Patent: Jan. 13, 2004

(54) PHARMACEUTICAL COMPOSITION WITH TUMOR NECROSIS FACTOR A AND 2-METHOXYESTRONE-3-0-SULPHAMATE FOR INHIBITION OF ESTRONE SULPHATASE

(75) Inventors: Michael John Reed, London (GB); Barry Victor Lloyd Potter, Bath (GB)

(73) Assignee: Sterix Limited, Oxford (GB)

( * ) Notice: Subject to any disclaimer, the term of this patent is extended or adjusted under 35 U.S.C. 154(b) by 0 days.

(21) Appl. No.: 09/724,986

(22) Filed: Nov. 28, 2000

Related U.S. Application Data

(63) Continuation-in-part of application No. PCT/GB99/01835, filed on Jun. 10, 1999.

(30) Foreign Application Priority Data

Jun. 10, 1998 (GB) .............................................. 9812535
Apr. 30, 1999 (GB) .............................................. 9910167

(51) Int. Cl.$^7$ ...................... A61K 45/00; A61K 31/165; C07K 14/52
(52) U.S. Cl. ...................... 424/85.1; 514/169; 514/171; 514/177; 514/12; 530/351; 530/828
(58) Field of Search ................................. 514/156, 169, 514/171, 177, 178, 208, 601, 607, 12; 424/85.1; 530/307, 828

(56) References Cited

U.S. PATENT DOCUMENTS 6,011,024 A * 1/2000 Reed et al. .................. 514/171
6,187,766 B1 * 2/2001 Reed et al. .................. 514/178

FOREIGN PATENT DOCUMENTS

| EP | 0934949 A1 | 8/1999 |
|---|---|---|
| GB | 2331988 | 6/1999 |
| WO | WO 93/05064 | 3/1993 |
| WO | WO 97/14712 | 4/1997 |
| WO | WO 98/24802 | 6/1998 |
| WO | WO 99/03876 | 1/1999 |
| WO | WO 99/33858 | 7/1999 |

OTHER PUBLICATIONS

Purohit et al., Biochem. Biophy. Res. Comm., vol. 261, pp. 214–217, 1999. (XP002121930).
Reed et al., J. Steroid. Biochem. Molec. Biol., vol. 53, No. 1–6, pp. 413–420, Jun. 1995. (XP002121931).
Li et al., Steroids: Structure, Function, and Regulation., US Elsevier Science Publishers, New York, NY. vol. 63, No. 7–8, Jul. 1998. (XP004134764).
Purohit et al., Journal of Endocrinology., vol. 150, pp. S65–S71, 1996. (XP002054919).
Purohit et al., J. Steroid. Biochem. Molec. Biol., vol. 64, no 5–6, pp. 269–275, 1998 (XP000852568).
Purohit et al., J. Steroid. Biochem. Molec. Biol., vol. 69, pp. 227–238, 1999. (XP000852540).
Simons M.H., Pharmaceutisch Weekblad., vol. 131, No. 19, pp. 549–550, 1996. (XP000852580).
Purohit et al., J. Steroid. Biochem. Molec. Biol., vol. 68, pp. 129–135, 1999. (XP000852538).
M.H. Simons, "Regulation and Inhibition of Oestrone Sulphatase Activity" Pharmaceutisch Weekblad, 131, 19, 1996. (XP000852580) (English translation).

* cited by examiner

Primary Examiner—Gary Kunz
Assistant Examiner—Jegatheesan Seharaseyon
(74) Attorney, Agent, or Firm—Frommer Lawrence & Haug; Thomas J. Kowalski

(57) ABSTRACT

A composition is described. The composition comprises i) a compound comprising a sulphamate group ("a sulphamate compound"); and ii) a biological response modifier.

14 Claims, 9 Drawing Sheets

PHARMACEUTICAL COMPOSITION WITH TUMOR NECROSIS FACTOR A AND 2-METHOXYESTRONE-3-0-SULPHAMATE FOR INHIBITION OF ESTRONE SULPHATASE

RELATED APPLICATIONS

This application is the continuation-in-part of PCT/GB99/01835, filed Jun. 10, 1999, designating the U.S. and published as WO 99/64013, with claims of priority from Great Britain application nos. 9812535.4, filed Jun. 10, 1998 and 9910167.7 filed Apr. 30, 1999. All of the foregoing applications, as well as all documents cited in the foregoing applications ("application documents") and all documents cited or referenced in application documents are hereby incorporated herein by reference. Also, all documents cited in this application ("herein cited documents") and all documents cited or referenced in herein cited documents are hereby incorporated herein by reference.

The present invention relates to a composition. In particular the present invention relates to a pharmaceutical composition—and to a class of compounds particularly useful in or as said composition.

Cancer remains a major cause of mortality in most Western countries. So far, evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore specific inhibitors of oestrogen biosynthesis are of potential value for the treatment of endocrine-dependent tumours.

Over the past two decades, there has been considerable interest in the development of inhibitors of the aromatase pathway which converts the androgen precursor androstenedione to oestrone. However, there is now evidence that the oestrone sulphatase ("E1-STS") pathway, i.e. the hydrolysis of oestrone sulphate ("E1S") to oestrone ("E1"), as opposed to the aromatase pathway, is the major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione and also by the fact that plasma E1S concentration in these aromatase inhibitor-treated patients remains relatively high. The long half-life of E1S in blood (10–12 h) compared with the unconjugated oestrogens (20 min) and high levels of steroid sulphatase activity in liver and, normal and malignant breast tissues, also lend support to this theory.

Singh et al (1997 J Steroid Biochem Mol Biol 61: 185–192), report that the major source of pro-inflammatory cytokines, such as TNF-α and IL-6 within breast tumours is not well understood but it is thought that tumour infiltrating macrophages and lymphocytes might play a role.

Singh et al (ibid) report that the release of cytokines, such as IL-6 by tumour cells is also associated with enhanced aromatase activity in breast tissue adjacent to the tumour. Singh et al (ibid) also report that both TNF-α and IL-6 inhibit the growth of MCF-7 breast cancer cells in vitro. In addition, TNF-α has an inhibitory effect on aromatase activity measured in cultured MCF-7 breast cancer cells. Apparently, these results contrast with the marked stimulatory effect that TNF-α has on fibroblasts derived from normal and malignant breast tissues (Macdiarmaid et al 1994 Molec. Cell Endoc. 106: 17–21). In addition, when TNF-α is combined with IL-6, the inhibitory effect on aromatase activity is enhanced. The synergistic inhibitory effect of IL-6 and TNF-α on aromatase activity in MCF-7 cells also contrasts to the synergistic stimulatory effect that these cytokines have on oestrone sulphatase and oestradiol dehydrogenase activities in these cells.

Singh et al (ibid) also report that a significant reduction in aromatase activity is observed when conditioned media (CM) from monocytes and lymphocytes of an immunosuppressed kidney transplant patient is added to fibroblast cultures from normal breast cells compared with CM from breast cancer cells. These results suggest that the reduced incidence of breast cancer in immunosuppressed kidney transplant patients could result from reduced cytokine production and thus decreased stimulation of oestrogen synthesis.

Previous studies have also shown that where CM from cultured breast cancer cells stimulates aromatase activity, this CM also stimulates the activities of two main enzymes, that is oestrone sulphatase and oestradiol dehydrogenase which are also involved in breast tumour oestrogen synthesis.

Thus, there appears to be a co-ordinated mechanism for regulating the synthesis of oestrogen within breast tumours that is controlled by cytokines. However, it has been postulated that any in vivo stimulatory effect of cytokines in inhibiting tumour growth may be outweighed by their stimulatory effect on enzyme activity associated with oestrogen synthesis (Duncan and Reed 1995 J Steroid Biochem Molec Biol 55:565–572).

Singh et al (ibid) state that while cytokines such as TNF-α and IL-6 have been shown to play an important role in regulating the activities of enzymes involved in oestrogen synthesis, it is likely that other cytokines and mediators of the inflammatory response are capable of modulating oestrogen synthesis in normal and malignant breast tissue.

Thus, cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

In fact, Singh et al (ibid) state that "by understanding the complex mechanisms which govern oestrogen synthesis, it should be possible to devise better preventative and therapeutic strategies" against cancers—especially breast cancer.

The present invention seeks to provide a composition suitable for use in the treatment of cancers and, especially, breast cancer.

According to a first aspect of the present invention there is provided a composition comprising i) a compound comprising a sulphamate group ("a sulphamate compound"); and ii) a biological response modifier.

According to a second aspect of the present invention there is provided the use of a composition according to the present invention in the manufacture of a medicament to prevent and/or inhibit tumour growth.

According to a third aspect of the present invention there is provided the use of a composition according to the present invention in the manufacture of a medicament to do any one or more of: prevent or suppress glucose uptake by a tumour; prevent and/or inhibit tumour angiogeneis; disrupt microtubules; induce apoptosis.

According to a fourth aspect of the present invention there is provided the use of a sulphamate compound comprising a steroidal component and an oxyhydrocarbyl group ("oxyhydrocarbyl steroidal sulpharnate compound") in the manufacture of a medicament to do any one or more of: prevent or suppress glucose uptake by a tumour; prevent and/or inhibit tumour angiogeneis; disrupt microtubules; induce apoptosis.

According to a fifth aspect of the present invention there is provided the composition of the present invention for use in medicine.

According to a sixth aspect of the present invention there is provided a method of treatment comprising administering to a subject in need of treatment a composition according to the present invention.

According to a seventh aspect of the present invention there is provided a method of treatment comprising administering to a subject in need of treatment a composition according to the present invention or an oxyhydrocarbyl steroidal sulphamate compound according to the present invention in order to prevent or suppress glucose uptake by a tumour; and/or prevent and/or inhibit tumour angiogeneis; and/or disrupt microtubules; and/or induce apoptosis.

According to an eighth aspect of the present invention there is provided a kit comprising a part i) containing a compound comprising a sulphamate group ("a sulphamate compound"); and a part ii) containing a biological response modifier. The parts of the kit may be independently held in one or more containers—such as bottles, syringes, plates, wells, blister pack etc.

The present invention is advantageous in that it provides a composition suitable for use in the treatment of cancers and, especially, breast cancer.

In addition, the present invention is advantageous in that it provides a compound that is suitable for use in the treatment of cancers such as breast cancer, ovarian cancer, endometrial cancer, sarcomas, melanomas, prostate cancer etc.—especially, breast cancer.

Another advantage of the compositions of the present invention is that they may be more potent in vivo than the sulphamate compounds alone or the biological response modifier alone. Moreover, in some aspects the combination of sulphamate compounds and the biological response modifier is more potent than one would expect from the potency of the compound alone i.e. this is a synergistic relationship between them.

In accordance with the present invention the composition of the present invention may comprise more than one biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. BRMs may play a role in modulating the immune and inflammatory response in disorders. Examples of BRMs include: Tumour Necrosis Factor (TNF), granulocyte colony stimulating factor, erythropoietin, insulin-like growth factor (IGF), epidermal growth factor (EGF), transforming growth factor (TGF), platelet-derived growth factor (PDGF), interferons (IFNs), interleukins, tissue plasminogen activators, P-, E- or L-Selectins, ICAM-1, VCAM, Selectins, addressins etc.

Preferably, the biological response modifier is a cytokine.

A cytokine is a molecule—often a soluble protein—that allows immune cells to communicate with each other. These molecules exert their biological functions through specific receptors expressed on the surface of target cells. Binding of the receptors triggers the release of a cascade of biochemical signals which profoundly affect the behaviour of the cell bearing the receptor (Poole, S 1995 TibTech 13: 81–82). Many cytokines and their receptors have been identified at the molecular level (Paul and Sedar 1994, Cell 76: 241–251) and make suitable molecules of therapeutic value as well as therapeutic targets in their own right.

More details on cytokines can be found in Molecular Biology and Biotechnology (Pub. VCH, Ed. Meyers, 1995, pages 202, 203, 394, 390, 475, 790).

Examples of cytokines include: interleukins (IL)—such as IL-1, IL-2, IL-3, IL4, IL-5, IL-6, IL-7, IL-8, IL-9, IL-10, IL-11, IL-12, IL-19; Tumour Necrosis Factor (TNF)—such as TNF-α; Interferon alpha, beta and gamma; TGF-β.

For the present invention, preferably the cytokine is tumour necrosis factor (TNF).

More preferably the cytokine is TNF-α.

TNF is a cytokine produced by macrophages and lymphocytes which mediates inflammatory and immunopathological responses. TNF has been implicated in the progression of diseases which include but are not limited to immunomodulation disorder, infection, cell proliferation, angiogenesis (neovascularisation), tumour metastasis, apoptosis, sepsis, and endotoxaemia.

The necrotising action of TNF in vivo mainly relates to capillary injury. TNF causes necrosis not only in tumour tissue but also in granulation tissue. It causes morphological changes in growth inhibition of and cytoxicity against cultured vascular endothelial cells (Haranka et al 1987 Ciba Found Symp 131: 140–153).

For the preferred aspect of the present invention, the TNF may be any type of TNF—such as TNF-α, TNF-β, including derivatives or mixtures thereof.

Teachings on TNF may be found in the art such as WO-A-98/08870 and WO-A-98/13348.

The TNF can be prepared chemically or it can be extracted from sources. Preferably, the TNF is prepared by use of recombinant DNA techniques.

With this aspect of the present invention the compositions of the present invention are more potent in vivo than the sulphamate compounds alone or TNF alone. Moreover, in some aspects the combination of sulphamate compounds and TNF is more potent than one would expect from the potency of the compound alone i.e. this is a synergistic relationship between them.

In accordance with the present invention the composition of the present invention may comprise more than one sulphamate compound.

The term "sulphamate compound" means a compound comprising at least one sulphamate group.

Preferably, if the sulphamate group on the sulphamate compound were to be replaced with a sulphate group to form a sulphate compound then the sulphate compound would be hydrolysable by a steroid sulphatase enzyme (E.C.3.1.6.2).

Preferably if the sulphamate group on the sulphamate compound were to be replaced with a sulphate group to form a sulphate compound and the sulphate compound were to be incubated with a steroid sulphatase enzyme (E.C.3.1.6.2) at a pH 7.4 and 37° C. it would provide a $K_m$ value of less than 50 mM.

Preferably if the sulphamate group on the sulphamate compound were to be replaced with a sulphate group to form a sulphate compound and the sulphate compound were to be incubated with a steroid sulphatase enzyme (E.C.3.1.6.2) at a pH 7.4 and 37° C. it would provide a $K_m$ value of less than 50 μM.

The term "sulphamate" includes an ester of sulphamic acid, or an ester of an N-substituted derivative of sulphamic acid, or a salt thereof.

Preferably, the sulphamate group of the sulphamate compound has the formula:

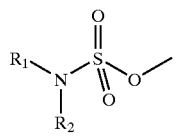

wherein each of $R_1$ and $R_2$ is independently selected from H or a hydrocarbyl group.

The term "hydrocarbyl group" as used herein means a group comprising at least C and H and may optionally comprise one or more other suitable substituents. Examples of such substituents may include halo-, alkoxy-, nitro-, a hydrocarbon group, an N-acyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

In one preferred embodiment of the present invention, the hydrocarbyl group is a hydrocarbon group.

Here the term "hydrocarbon" means any one of an alkyl group, an alkenyl group, an alkynyl group, an acyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Preferably, $R_1$ and $R_2$ are independently selected from H or alkyl, cycloalkyl, alkenyl and aryl, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl, N-acyl, or N-aryl substituents, preferably containing or each containing a maximum of 10 carbon atoms. When $R_1$ and/or $R_2$ is alkyl, the preferred values are those where $R_1$ and $R_2$, are each independently selected from lower alkyl groups containing from 1 to 5 carbon atoms, that is to say methyl, ethyl, propyl etc. Preferably $R_1$ and $R_2$ are both methyl. When $R_1$ and/or $R_2$ is aryl, typical values are phenyl and tolyl (—$PhCH_3$; o-, m- or p-). Where $R_1$. and $R_2$ represent cycloalkyl, typical values are cyclopropyl, cyclopentyl, cyclohexyl etc. When joined together $R_1$ and $R_2$, typically represent an alkylene group providing a chain of 4 to 6 carbon atoms, optionally interrupted by one or more hetero atoms or groups, e.g. —O— or —NH— to provide a 5-, 6- or 7- membered heterocycle, e.g. morpholino, pyrrolidino or piperidino.

Within the values alkyl, cycloalkyl, alkenyl, acyl and aryl we include substituted groups containing as substituents therein one or more groups which do not interfere with the sulphatase inhibitory activity of the compound in question. Exemplary non-interfering substituents include hydroxy, amino, halo, alkoxy, alkyl and aryl. A non-limiting example of a hydrocarbyl group is an acyl group.

In some preferred embodiments, at least one of $R_1$ and $R_2$ is H.

Preferably the sulphamate compound is a cyclic compound. In this regard, the sulphamate compound can be a single ring compound or a polycyclic compound. Here, the term "polycyclic" includes fused and non-fused ring structures including combinations thereof.

Thus, preferably the sulphamate compound is of the formula $$E-G$$

wherein E is a sulphamate group and wherein G is a cyclic group.

The cyclic group may be a single ring or it is a polycylic ring structure.

In one aspect, the cyclic group may contain any one or more of C, H, O, N, P, halogen (including Cl, Br and I), S and P.

At least one of the cyclic groups may be a heterocyclic group (a heterocycle) or a non-heterocyclic group.

At least one of the cyclic groups may be a saturated ring structure or an unsaturated ring structure (such as an aryl group).

Preferably, at least one of the cyclic groups is an aryl ring.

Preferably, the sulphamate group is linked to the aryl ring.

If the cyclic group is polycyclic some or all of the ring components of the sulphamate compound may be fused together or joined via one or more suitable spacer groups.

Thus, in accordance with one aspect of the present invention, preferably the sulphamate compound is a polycyclic compound.

Preferably the polycyclic compound will contain, inclusive of all substituents, no more than 50 about carbon atoms, more usually no more than about 30 to 40 carbon atoms.

The polycyclic compound can comorise at least two ring components, or least three ring components, or least four ring components.

Preferably, the polycyclic compound comprises four ring components.

Preferred polycyclic compounds have a steroidal ring component—that is to say a cyclopentanophenanthrene skeleton, or bio-isosteres thereof.

As is well known in the art, a classical steroidal ring structure has the generic formula of:

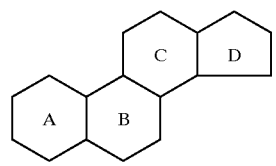

In the above formula, the rings have been labelled in the conventional manner.

An example of a bio-isostere is when any one or more of rings A, B, C and D is a heterocylic ring and/or when any one or more of rings A, B, C and D has been substituted and/or when any one or more of rings A, B, C and D has been modified; but wherein the bio-isostere in the absence of the sulphamate group has steroidal properties.

In this regard, the structure of a preferred polycyclic compound can be presented as:

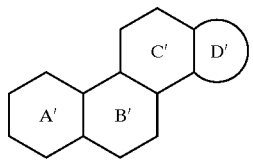

wherein each ring A', B', C' and D' independently represents a heterocyclic ring or a non-heterocylic ring, which rings may be independently substituted or unsubstituted, saturated or unsaturated.

By way of example, any one or more of rings A', B', C' and D' may be independently substituted with suitable groups—such as an alkyl group, an allyl group, an hydroxy group, a halo group, a hydrocarbyl group, an oxyhydrocarbyl group etc.

An example of D' is a five or six membered non-heterocyclic ring having at least one substituent.

In one preferred embodiment, the ring D' is substituted with a ethinyl group.

If any one of rings A', B', C' and D' is a heterocyclic ring, then preferably that heterocylic ring comprises a combination of C atoms and at least one N atom and/or at least one O atom. Other heterocyclic atoms may be present in the ring.

Examples of suitable, preferred steroidal nuclei rings A'–D' of the compounds of the present invention include rings A–D of oestrone and dehydroepiandrosterone.

Preferred steroidal nuclei rings A'–D' of the compounds of the present invention include rings A–D of:
Oestrones and Substituted Oestrones, Viz:
  oestrone
  2-OH-oestrone
  2-alkoxy-oestrone (such as $C_{1-6}$ alkoxy-oestrone, such as 2-methoxy-oestrone)
  4-OH-oestrone
  6α-OH-oestrone
  7α-OH-oestrone
  16α-OH-oestrone
  16β-OH-oestrone
Oestradiols and Substituted Oestradiols, Viz:
  2-OH-17β-oestradiol
  2-alkoxy-17β-oestradiol (such as $C_{1-6}$ alkoxy-17β-oestradiol, such as 2-methoxy-17β-oestradiol)
  4-OH-17β-oestradiol
  6α-OH-17β-oestradiol
  7α-OH-17β-oestradiol
  2-OH-17α-oestradiol
  2-alkoxy-17α-oestradiol (such as $C_{1-6}$ alkoxy-17α-oestradiol, such as 2-methoxy-17α-oestradiol)
  4-OH-17α-oestradiol
  6α-OH-17α-oestradiol
  7α-OH-17α-oestradiol
  16α-OH-17α-oestradiol
  16α-OH-17β-oestradiol
  16β-OH-17α-oestradiol
  16β-OH-17β-oestradiol
  17α-oestradiol
  17β-oestradiol
  17α-ethinyl-17β-oestradiol
  17β-ethinyl-17α-oestradiol
Oestriols and Substituted Oestriols, Viz:
  oestriol
  2-OH-oestriol
  2-alkoxy-oestriol (such as $C_{1-6}$ alkoxy-oestriol, such as 2-methoxy-oestriol)
  4-OH-oestriol
  6α-OH-oestriol
  7α-OH-oestriol
Dehydroepiandrosterones and Substituted Dehydroepiandrosterones, Viz:
  dehydroepiandrosterones
  6α-OH-dehydroepiandrosterone
  7α-OH-dehydroepiandrosterone
  16α-OH-dehydroepiandrosterone
  16β-OH-dehydroepiandrosterone In general terms the ring system A'B'C'D' may contain a variety of non-interfering substituents. In particular, the ring system A'B'C'D' may contain one or more hydroxy, alkyl especially lower ($C_1$–$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc., aLkinyl, e.g. ethinyl, or halogen, e.g. fluoro substituents.

In an alternative embodiment, the polyclic compound may not contain or be based on a steroid nucleus. In this regard, the polyclic compound may contain or be based on a non-steroidal ring system—such as diethylstilboestrol, stilboestrol, coumarins, and other ring systems. Other suitable non-steroidal compounds for use in or as the composition of the present invention may be found in U.S. Pat. No. 5,567,831.

In formula (I), the at least one sulphamate group is attached to any one or more of the ring components.

Preferably, the polycyclic compound has a steroidal structure and wherein the sulphamate group is attached to the A ring.

Preferably, the sulphamate group is attached to the 3 position of the A ring.

Preferably the sulphamate compound comprises at least one oxyhydrocarbyl group.

A preferred sulphamate compound is an oxyhydrocarbyl steroidal sulphamate compound (i.e. a sulphamate compound comprising a steroidal component and an oxyhydrocarbyl group).

In one embodiment, preferably, the sulphamate compound is an oxyhydrocarbyl steroidal sulphamate compound wherein the sulphamate group is in the 3 position on the steroidal component and/or the oxyhydrocarbyl group is in the 2-position position on the steroidal component.

In one embodiment, preferably, the sulphamate compound is an oxyhydrocarbyl derivative of oestrone sulphamate.

In one embodiment, preferably, the sulphamate compound is an oxyhydrocarbyl derivative of oestrone-3-O-sulphamate.

In one embodiment, preferably, the sulphamate compound is a $C_{1-6}$ (such as a $C_{1-3}$) alkoxy derivative of oestrone-3-O-sulphamate.

In one embodiment, preferably, the sulphamate compound is a 2-$C_{1-6}$ (such as a $C_{1-3}$) alkoxy derivative of oestrone-3-O-sulphamate.

In one embodiment, preferably, the sulphamate compound is 2-methoxyoestrone-3-O-sulphamate.

The term "oxyhydrocarbyl group" as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group.

Thus, the oxyhydrocarbyl group may contain hetero atoms. Suitable hetero atoms will be apparent to those skilled in the art and include, for instance, sulphur and nitrogen.

In one preferred embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Preferably the oxyhydrocarbyl group is of the formula $C_{1-6}O$ (such as a $C_{1-3}O$).

If the sulphamate compound comprises a steroidal nucleus, preferably the A ring has an oxyhydrocarbyl group at the 2 position.

More preferably the group $C_{1-6}O$ is attached to the 2 position of the A ring of a steroidal nucleus.

Preferably, the oxyhydrocarbyl group is an alkoxy.

The alkyl group of the alkoxy substituent is preferably a lower alkyl group containing from 1 to 5 carbon atoms, that is to say methyl, ethyl, propyl etc. Preferably, the alkyl group is methyl.

Thus, in a preferred embodiment, if the sulphamate compound comprises a steroidal nucleus the A ring has an methoxy substituent at the 2 position.

Preferably the sulphamate compound is suitable for use as an inhibitor of oestrone sulphatase (E.C. 3.1.6.2).

In one preferred embodiment of the present invention, preferably the sulphamate compound is non-oestrogenic. The term "non-oestrogenic" means exhibiting no or substantially no oestrogenic activity.

In one preferred embodiment of the present invention, preferably the sulphamate compound are not capable of being metabolised to compounds which display or induce hormonal activity.

In one preferred embodiment of the present invention, preferably the composition of the present invention is orally active.

The present invention is based on the highly surprising finding that the combination of a sulphamate compound and a biological response modifier provides an effective treatment of cancer.

More in particular, we have surprisingly found that the composition of the present invention—and 2-methoxyoestrone-3-O-sulphamate—can prevent or suppress glucose uptake by a tumour and/or prevent and/or inhibit tumour angiogeneis and/or disrupt microtubules and/or induce apoptosis.

In this respect, microtubules, together with microfilaments and intermediate filaments form part of the cytoskeletal system of a cell. Microtubules are responsible for many of cell movements-examples include the beating of cilia and flagella and the transport of membrane vesicles in the cytoplasm. All these movements result from the polymerisation and depolymerisation of microtubules or the actions of the microtubule motor proteins dynein and kinesins. Some other cell movements, such as the alignment and separation of chromosomes during meiosis and mitosis result from both mechanisms. Microtubules also direct cell movement but in some cases, microtubules serve purely structural functions.

A microtubule is composed of subunits that are heterodimers of $\alpha$-tubulin and $\beta$-tubulin monomers. There are two populations of microtubules: stable, long-lived microtubules and dynamic, short lived microtubules. Dynamic microtubules are found when the microtubule structures need to assemble and dissemble quickly. For example, during mitosis, the cytosolic microtubule network characteristic of interphase cells disappears and the tubulin from it is used to form the spindle apparatus which partitions chromosomes equally to the daughter cells. When mitosis is complete, the spindle disassembles and the interphase microtubule network reforms.

Drugs that inhibit mitosis provide a useful means to manipulate the microtubules in a cell. Three drugs: colchicine, vinblastine and taxol—all purified from plants— have proved to be very powerful probes of microtubule function partly because they bind only to tubulin or microtubules and not to other proteins and also because their concentrations in cells can be easily controlled.

Because of their effects on mitosis, microtubule inhibitors have been widely used to treat illness and more recently as anticancer agents, since blockage of spindle formation will preferentially inhibit rapidly dividing cells like cancer cells. A highly effective anti-ovarian cancer agent is taxol. In ovarian cancer cells, which undergo rapid cell divisions, mitosis is blocked by taxol treatment while other functions carried out by intact microtubules are not affected. A comprehensive review of microtubules can be found in "Molecular Cell Biology" (Ed: Lodish et al 1995 WH Freeman and Co. New York pp 1051–1122).

Apoptosis is induced by MT-targeting drugs, a process which may involve the phosphorylation (and inactivation) of the apoptosis regulator, the bcl-2 protein (Halder, Cancer Res. 57: 229, 1997).

Preferably the composition of the present invention further comprises a pharmaceutically acceptable carrier, diluent, or excipient.

For pharmaceutical administration, the composition of the present invention can be formulated in any suitable manner utilising conventional pharmaceutical formulating techniques and pharmaceutical carriers, adjuvants, excipients, diluents etc.—such as those for parenteral administration. Approximate effective dose rates are in the range 100 to 800 mg/day depending on the individual activities of the compounds in question and for a patient of average (70 Kg) bodyweight. More usual dosage rates for the preferred and more active compositions will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of composition per unit dose. Alternatively and preferably the compositions will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

The composition or compound of the present invention may be administered in any suitable manner—such as any one or more of oral administration, topical administration (such as by means of a patch), parenteral administration, rectal administration or by inhalation spray.

In the method of treatment, the subject is preferably a mammal, more preferably a human. For some applications, preferably the human is a woman.

For particular applications, it is envisaged that the compositions of the present invention may be used in combination therapies, either with another sulphatase inhibitor, or, for example, in combination with an aromatase inhibitor, such as for example, 4-hydroxyandrostenedione (4-OHA).

In accordance with the present invention, the components of the composition can be added in admixture, simultaneously or sequentially. Furthermore, in accordance with the present invention it may be possible to form at least a part of the composition in sit (such as in vivo) by inducing the expression of—or increasing the expression of—one of the components. For example, it may be possible to induce the expression of—or increase the expression of—the biological response modifier, such as TNF. By way of example, it may be possible to induce the expression of—or increase the expression of—TNF by adding bacterial lipopolysaccharide (LPS) and muramyl dipeptide (MDP). In this regard, bacterial LPS and MDP in combination can stimulate TNF production from murine spleen cells in vitro and tumour regression in vivo (Fuks et al Biull Eksp Biol Med 1987 104: 497–499).

In addition, the present invention contemplates the composition of the present invention further comprising an inducer of the biological response modifier—such as in vivo inducer of the biological response modifier.

The present invention also contemplates the combination of an oxyhydrocarbyl steroidal sulphamate compound according to the present invention (such as 2-methoxyoestrone-3-O-sulphamate) with an inducer of a biological response modifier—such as an in vivo inducer of an in situ biological response modifier.

Examples of suitable sulphamate compounds for use in or as the composition of the present invention, or examples of suitable compounds that can be converted to suitable sulphamate compounds for use in or as the composition of the present invention, can be found in the art—such as PCT/GB92/01587, PCT/GB97/03352, PCT/GB97/00444, GB9725749.7, GB9725750.5, U.S. Pat. No. 5567831, U.S. Pat. No. 5677292, U.S. Pat. No. 5567831, WO-A-96/05216, and WO-A-96/05217, U.S. Pat. Nos. 6,083,978, 6,017,904, 6,011,024, 5,861,390, 5,830,886, 5,616,574, and 5,604,215, and U.S. applications Ser. Nos. 09/638,315, 09/638,314, 09/125,255, 09/319,213, 09/561,453, 09/572,246 and 09/572,237; and each of the foregoing patents and applications, and all documents cited or referenced in each of the foregoing patents and applications including during any prosecution ("appln. cited documents') and all documents referenced or cited in the appln. cited documents, are hereby incorporated herein by reference.

By way of example, PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters. Examples of such inhibitors are sulphamate ester derivatives of steroids.

A compound suitable for use in the present invention—which is also a preferred compound of PCT/GB92/01587—is oestrone-3-sulphamate (otherwise known as "EMATE"), which has the following structure:

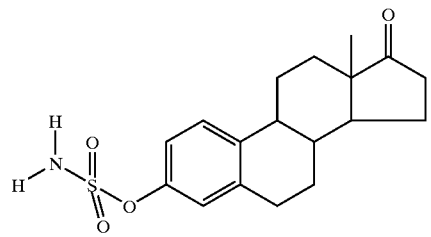

It is known that EMATE is a potent E1-STS inhibitor as it displays more than 99% inhibition of E1-STS activity in intact MCF-7 cells at 0.1 $\mu$M. EMATE also inhibits the E1-STS enzyme in a time—and concentration-dependent manner, indicating that it acts as an active site-directed inactivator.

Preferably, the A ring has a substituent that is an oxyhydrocarbyl group.

Another compound suitable for use in the present invention has at least the following skeletal structure:

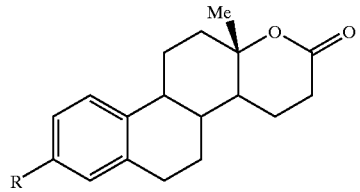

wherein R denotes a sulphamate group as described above.

Preferably, R is the above-mentioned preferred formula for the sulpharnate group. In this regard, it is preferred that at least one of $R_1$ and $R_2$ is H.

Preferably, the A ring has a substituent that is an oxyhydrocarbyl group.

Another compound suitable for use in the present invention has at least the following skeletal structure:

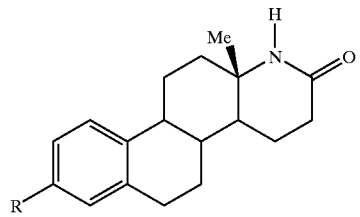

wherein R denotes a sulphamate group as described above.

Preferably, R is the above-mentioned preferred formula for the sulphamate group. In this regard, it is preferred that at least one of $R_1$ and $R_2$ is H.

Preferably, the A ring has a substituent that is an oxyhydrocarbyl group.

In accordance with a preferred aspect of the present invention, if the sulphamate group of the compound were to be replaced with a sulphate group to form a sulphate compound then that sulphate compound would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 50 m Moles when incubated with steroid sulphatase EC 3.1.6.2 at pH 7.4 and 37° C.

In another preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a $K_m$ value of less than 50 μMoles when incubated with steroid sulphatase EC 3.1.6.2 at pH 7.4 and 37° C.

In a further aspect the present invention provides use of a sulphamate compound for the manufacture of a medicament to prevent and/or inhibit tumour growth; wherein the sulphamate compound is suitable for use as an inhibitor of oestrone sulphatase (E.C. 3.1.6.2); wherein the compound is a polycyclic compound having a steroidal structure, or a bio-isostere thereof; wherein the polycyclic compound comprises at least one sulphamate group attached to the A ring; and wherein the polycyclic compound comprises at least one oxyhydrocarbyl group attached to the A ring.

We have found that sulphamate compounds having an oxyhydrocarbyl substituent on the A ring are potent (and in some cases highly potent) in (i) preventing and/or inhibiting glucose uptake of a tumour and/or (ii) preventing and/or inhibiting tumour angiogeneis and/or (iii) disrupting microtubules and/or iv) inducing apoptosis.

Thus in a further aspect the present invention provides use of a sulphamate compound for the manufacture of a medicament to prevent and/or inhibit glucose uptake of a tumour and/or to prevent and/or inhibit tumour angiogenesis and/or to disrupt microtubules and/or induce apoptosis; wherein the sulphamate compound is suitable for use as an inhibitor of oestrone sulphatase (E.C. 3.1.6.2); wherein the compound is a polycyclic compound having a steroidal structure or a bio-isostere thereof; wherein the polycyclic compound comprises at least one sulphamate group attached to the A ring; and wherein the polycyclic compound comprises at least one oxyhydrocarbyl group attached to the A ring.

A preferred sulphamate compound of the present invention has the formula:

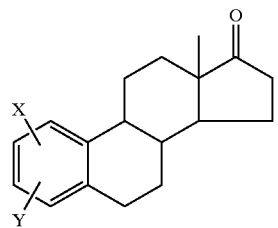

wherein X is an oxyhydrocarbyl group; and Y is a sulphamate group; and
 wherein rings A, B, C and D are independently optionally substituted.
 Preferably Y is in the 3-position.
 Preferably X is in the 2-position.
 For the present invention, preferably the sulphamate compound is an oxyhydrocarbyl steroidal sulphamate compound, in particular 2-methoxyoestrone-3-O-sulphamate, or a pharmaceutically active salt thereof, including analogues thereof.

2-methoxyoestrone-3-O-sulphamate is an analogue of EMATE—and can be called 2-methoxy EMATE.

2-methoxy EMATE is the sulphamoylated derivative of a naturally occurring oestrogen metabolite, 2-methoxyoestrone. This compound is formed in the liver by the hydroxylation of oestrone by a 2-hydroxylase, with subsequent metabolism to the methoxy derivative by catechol oestrogen methyl transferase.

2-methoxy EMATE has the formula presented as formula below:

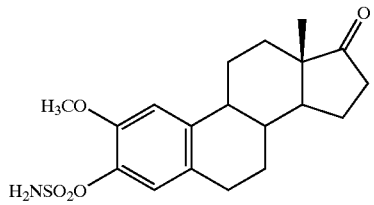

2-methoxy EMATE is believed to act in vivo, at least in part, by inhibiting tumour angiogenesis.

Thus, in a highly preferred embodiment the sulphamate compound is an oxyhydrocarbyl steroidal sulphamate compound, in particular 2-methoxyoestrone-3-O-sulphamate (2-methoxy EMATE).

In this regard, we have found that a sulphamate compound having a $C_{1-6}$ (such as a $C_{1-3}$) alkoxy substituent at the 2 position of the A ring, in particular 2-methoxy EMATE, is highly potent in preventing and/or inhibiting growth of tumours.

The present invention also provides compositions/ compounds which:
 cause inhibition of growth of oestrogen receptor positive (ER+) and ER negative (ER–) breast cancer cells in vitro by induction of apoptosis.
 cause regression of nitroso-methyl urea (NMU)—induced mammary rumours in intact animals (i.e. not ovariectomised).
 inhibit the uptake of glucose in cancer cells, in particular in breast cancer cells and breast tumour-derived fibroblasts.
 induce apoptosis.
 disrupt microtubules (Mts).
 act in vivo by inhibiting angiogenesis.

The sulphamate compounds of the present invention may be prepared by reacting an appropriate alcohol with the appropriate sulfamoyl chloride, $R_1R_2NSO_2Cl$. Preferred conditions for carrying out the reaction are as follows. Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography. Preferably, the alcohol is derivatised, as appropriate, prior to reaction with the sulfamoyl chloride. Where necessary, functional groups in the alcohol may be protected in known manner and the protecting group or groups removed at the end of the reaction.

In summation, the present invention provides compositions for use in treatment of tumours and pharmaceutical compositions containing them.

The present invention will now be described only by way of example, in which reference, in which reference shall be made to the following Figures.

FIG. 1 is a photographic plate (Plate 1) depicting MCF-7 (ER+) breast cancer cells used as controls Less than 1% of the cells present were apoptotic.

FIG. 2 is a photographic plate (Plate 2) depicting MCF-7 cells 72 hours after treatment with 5 $\mu$M of 2-methoxy EMATE. More than 90% of the cells present were apoptotic.

FIG. 3 is a photographic plate (Plate 3) depicting MDA-MB231 (ER−) breast cancer cells used as controls Less than 2% of the cells present were apoptotic.

FIG. 4 is a photographic plate (Plate 4) depicting MDA-MB-231 cells 24 hours after treatment with 1 $\mu$M of 2-methoxy EMATE. More than 50% of the cells present were apoptotic.

FIG. 5 is a photographic plate (Plate 5) depicting Breast tissue-derived fibroblasts (BTFs) used as controls. Less than 1% of the cells present were apoptotic.

FIG. 6 is a photographic plate (Plate 6) depicting BTFs 24 hours after treatment with 1 $\mu$M of 2-methoxy EMATE. More than 30% of the cells present were apoptotic FIG. 7 is a photographic plate (Plate 7) depicting MCF-7 cells following treatment with TNF$\alpha$ at a dose of 10 ng/ml. Less than 1% of the cells present were apoptotic FIG. 8 is a photographic plate (Plate 8) depicting MCF-7 cells treated with 2-methoxy EMATE at 1 mM and TNF$\alpha$ at 10 ng/ml. More than 90% of the cells present were apoptotic.

Synthesis of 2-methoxyoestrone-3-O-Sulphamate (2-Methoxy EMATE)

Figure 1:
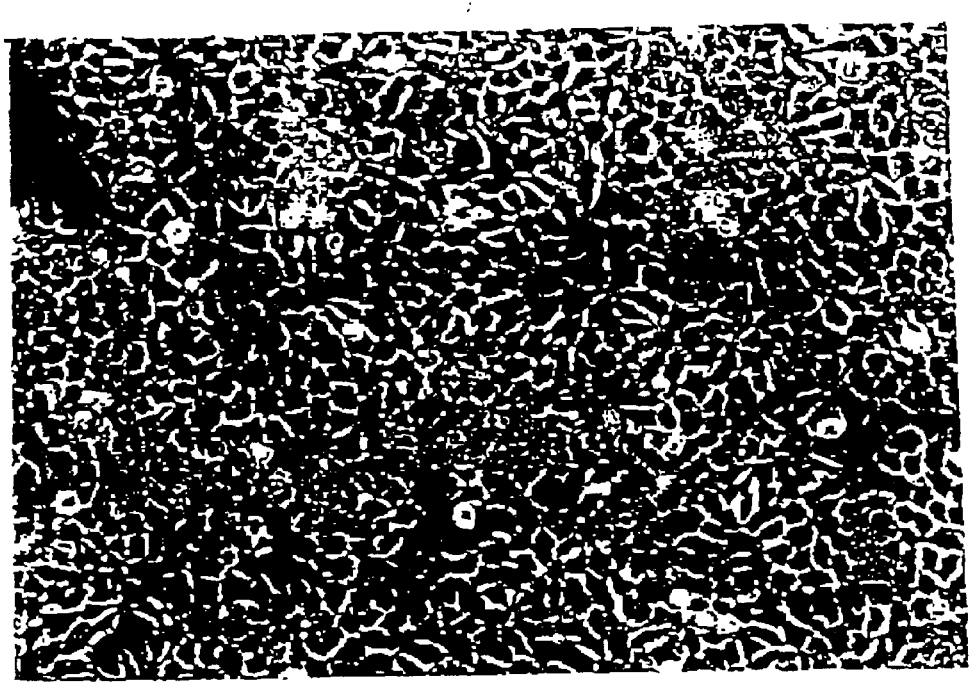
Figure 2:
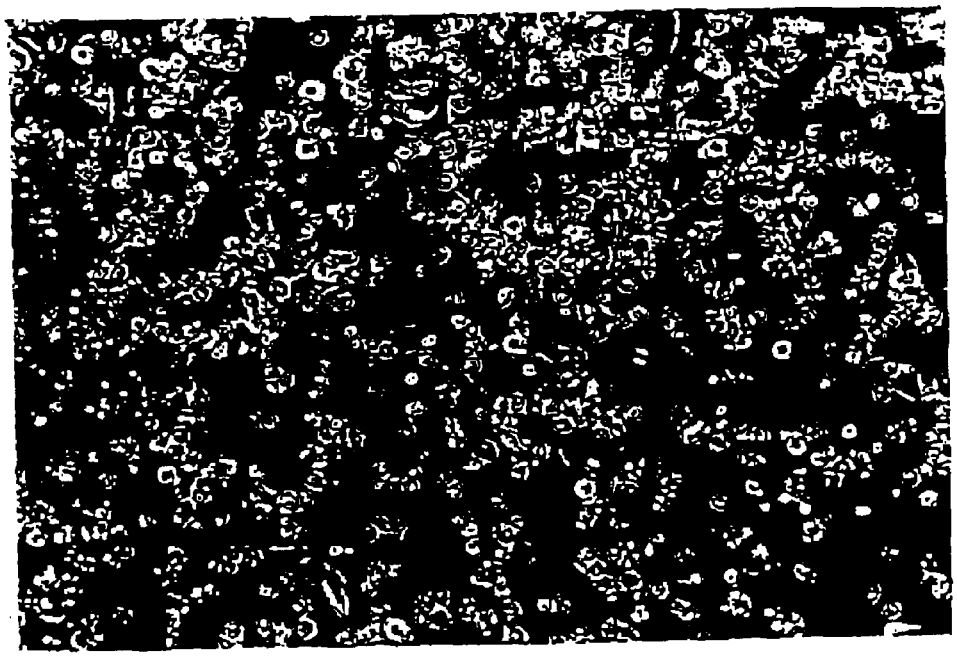
Figure 3:
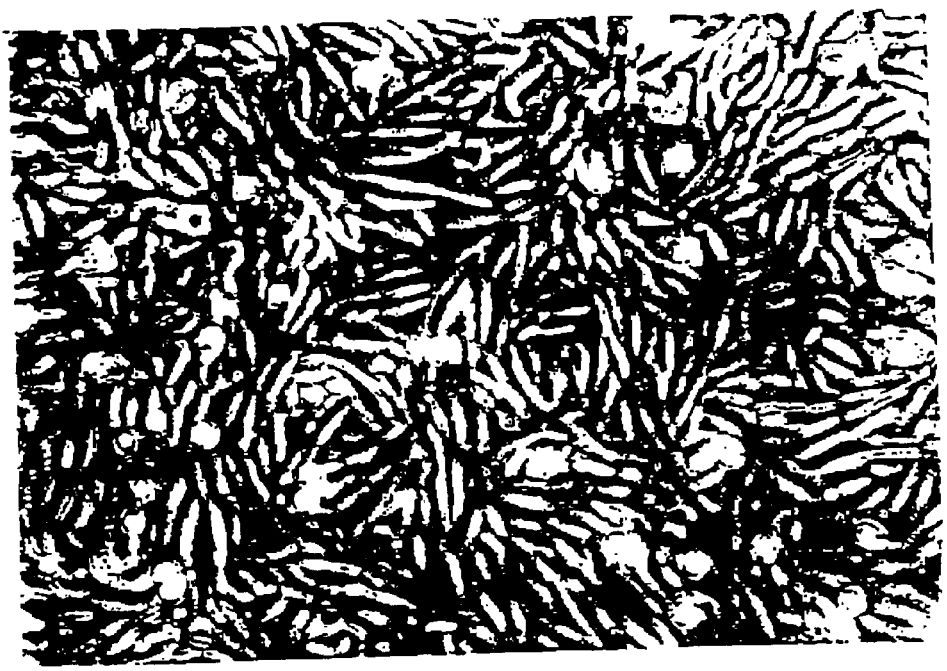
Figure 4:
Figure 5:
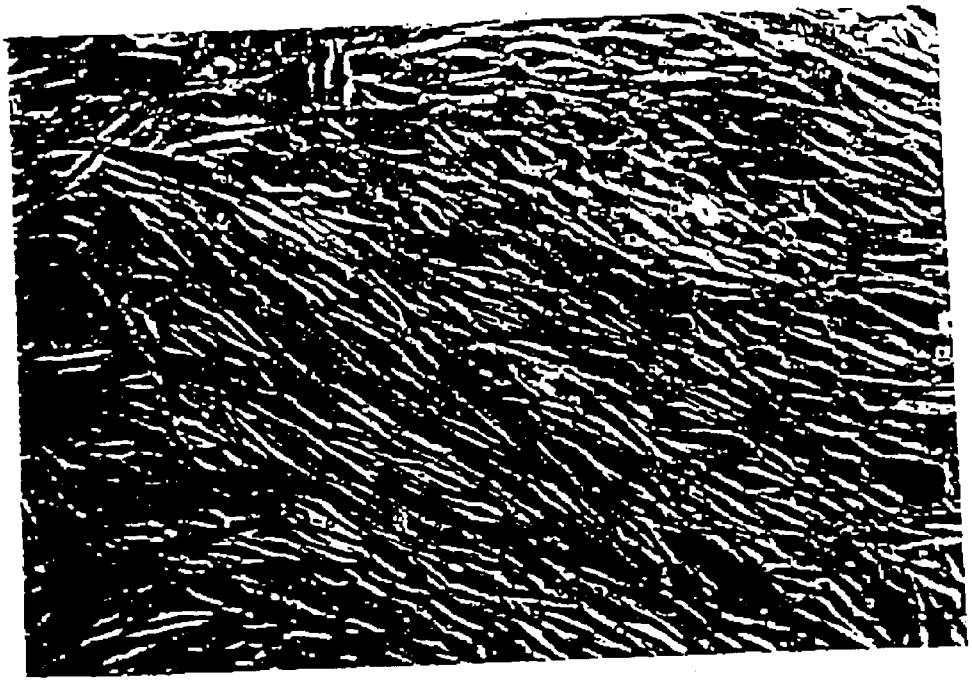
Figure 6:
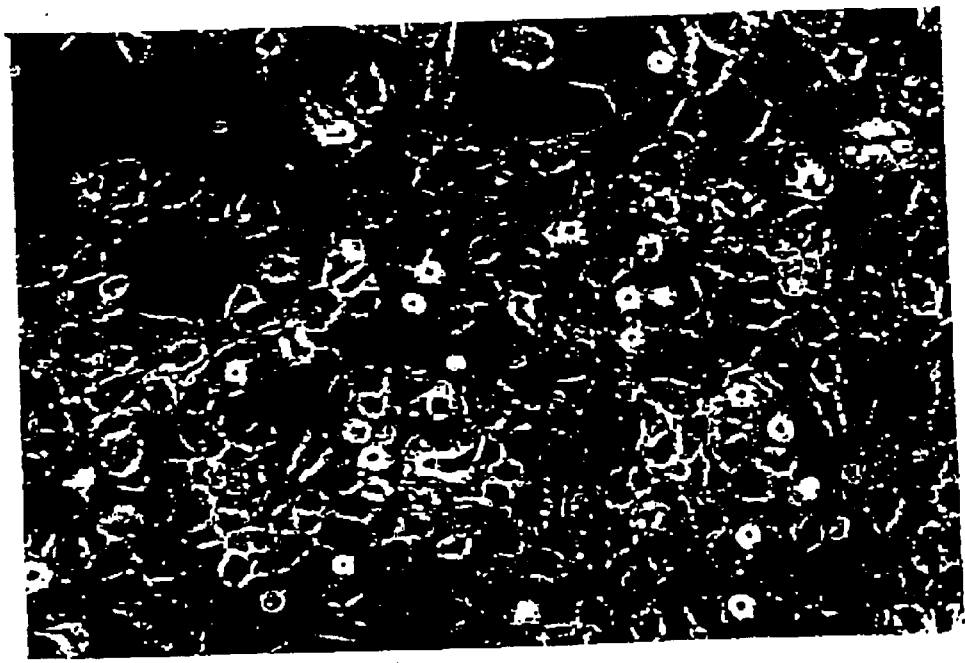
Figure 7:
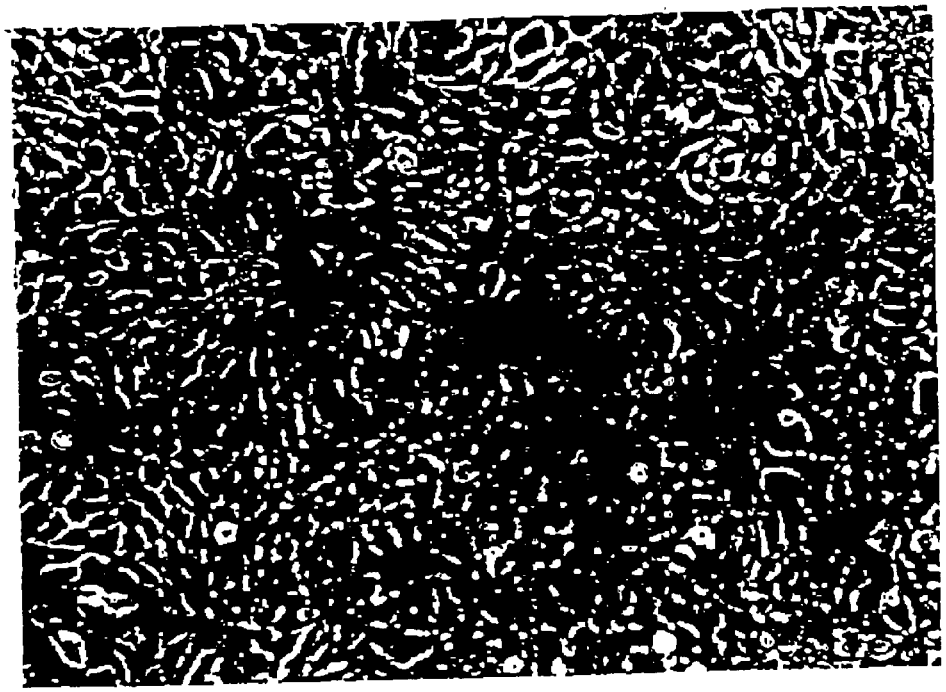

2-methoxy EMATE was synthesised by treating a solution of 2 methoxyoestrone in anhydrous dimethylformamide with sodium hydride at 0° C. After evolution of hydrogen had ceased sulphamoyl chloride (2 equiv.) was added and the reaction mixture was allowed to warm to room temperature overnight. The compound was purified by silica gel flash chromatography, was a single pure spot by TLC and exhibited satisfactory spectroscopic and microanalytical data.

In this regard, 2-methoxy oestrone (75 mg, 0.250 mmol) gave a crude product (103 mg) which was fractionated on silica (50 g) with chloroform/acetone (8:1) and upon evaporation the second fraction gave a pale white residue (83 mg, 81%) which was recrystallized in ethylacetate/hexane (1:2) to give 1 as white crystals (69 mg) .m.p=177–180° C., $R_f$s=0.29 and 0.54 for chloroform/ acetone 8:1 and 4:1 respectively and 0.46 and 0.31 for ethylacetate/hexane 2:1 and 1:1 respectively. vmax (KBr) 3400, 3300 (—NH$_2$), 1610 (C=O), and 1380 (—SO$_2$N-) cm$^{-1}$. $\delta_H$ (CDCl$_3$) 0.922 (3H, s, C-18-CH$_3$) 1.24–2.87 (15H, m), 3.88 (3H, s, C-2-OCH$_3$), 5.0 (2H, br s, exchanged with D$_2$O,-SO$_2$NH$_2$), 6.93 (1H, s, C-1-H) and 7.06 (1H, s, C-4-H). MS: M/z (+ve ion FAB in m-NBA, rel. intensity) 379.1 [100, (M)$^+$], 300.0 [25, (M-SO$_2$NH$_2$)$^+$]. MS: m/z (—ve ion FAB in m-NBA, rel. intensity) 378.0 [100, (M-H)]. Acc. MS: m/z (FAB$^+$)= 380.1515 C$_{19}$H$_{26}$NO$_5$S requires 380.1532 Found C, 60.0; H, 6.7; N, 3.67; C$_{19}$H$_{25}$NO$_5$S requires C, 60.14; H, 6.64; N, 3.69%.

EXPERIMENTAL STUDIES

1. Effect of 2-methoxy EMATE on Cell Growth and Apoptosis

Apoptotic cells undergo rounding, become detached from their neighbours and are easily detected by light microscopy. An estimate of the proportion of apoptotic cells was made by counting the number of rounded cells in ten microscopic fields. Representative photomicrographs of control and treated cells are shown.

| Plate No. | % Apoptotic Cells |
| --- | --- |
| Plate 1 | <1 |
| MCF-7 (ER+) breast cancer cells. Controls. | |
| Plate 2 | >90 |
| MCF-7 cells + 2-methoxy EMATE (5 $\mu$M, 72 h) | |
| Plate 3 | <2 |
| MDA-MB231 + (ER−) breast cancer cells. Controls. | |
| Plate 4 | >50 |
| MDA-MB-231 + 2-methoxy EMATE (1 $\mu$M, 24 h) | |
| Plate 5 | <1 |
| Breast tissue-derived fibroblasts (BTFs). Controls. | |
| Plate 6 | >30 |
| BTFs + 2-methoxy EMATE (1 $\mu$M, 24 h) | |

2. Effect of 2-methoxy EMATE on Tumour Growth in Vivo

To examine the ability of 2-methoxy EMATE to inhibit tumour growth in animals, Ludwig rats were obtained from Harlan-Olac (UK) Ltd after induction of mammary tumours with nitroso-methyl urea (NMU). For tumour induction 50-day-old rats were injected via the tail vein with NMU (50 mg/kg) receiving 3 injections at 14-day intervals. Tumour development was monitored and upon reaching 1.0–1.5 cm in diameter animals were given 2-methoxy EMATE (20 mg/kg/d for 11 days) or vehicle (propylene glycol).

Tumours (Vol D$_{11}$) in animals receiving vehicle only for 11 days remained static or increased by 109% compared with tumour volumes at the start of the treatment period (Vol D$_0$) (Table I). In contrast in 2/3 animals treated with 2-methoxy EMATE tumours showed complete regression within the 11-day treatment period. These are intact animals and therefore still produce oestrogen from their ovaries, but 2 months later no recurrence of tumour growth has been detected. The tumour in the 3rd animal was larger and may have required a higher dose/longer period of treatment to cause regression.

TABLE I

Effect of 2-methoxy EMATE on in vivo tumour growth

| Controls | (Vol $D_{11}$/Vol $D_0$ %) | 2-methoxy EMATE (Vol $D_{11}$/Vol $D_0$ %) |
| --- | --- | --- |
| 1 | 100 | <10 |
| 2 | 155 | <13 |
| 3 | 209 | 144 (no response) |

3. Effect of 2-methoxy EMATE on Glucose Uptake

MCF-7 cells or fibroblasts were seeded into 24- well tissue culture plates and grown until approximately 80% confluent. Cells were washed twice with phosphate-buffered saline (PBS, 5 ml). 2-methoxy EMATE was added in glucose-free RPMI culture medium (1 ml) containing 2-deoxyglucose (1 μCi, Amersham International). Cells were incubated for 15 min at 37° C. after which they were washed twice with cold (0–4° C.) PBS (5 ml). Cells were solubilized using 0.2% Triton X-100 in 0.01M NaOH (1 ml): Cell associated radioactivity was determined by liquid scintillation spectrometry. Replicate tissue culture plates were seeded with MCF-7 cells or fibroblasts to determine cell numbers.

TABLE II

Inhibition of Glucose Uptake

| | % Controls |
| --- | --- |
| MCF-7 cells + 2-methoxy EMATE (10 μM) | 51 |
| Breast tumour-derived fibroblasts + 2-methoxy EMATE (10 μM) | 36 |

At 10 μM 2-methoxy EMATE resulted in a significant (49% and 74% respectively) inhibition of glucose uptake by MCF-7 cells and fibroblasts respectively.

4. Effect of 2-methoxy EMATE on Glucose Uptake

For uptake assays cells were plated into 12-well multi-well plates and grown to confluence. Cells were washed with PBS and incubated for 15min in incubation buffer containing 1 μCi 2-deoxy-D-[1-$^3$H] glucose (26.2Ci/mmol, NEN-Dupont. UK) per well in the absence or presence of potential inhibitors (0.1–10 μM). Uptake was terminated by washing the cells in cold (4° C.) PBS. The cells were solubilized in Triton-x in 0.01M NaOH and processed for liquid scintillation counting. Cell number was determined using parallel wells and counting as described below under Cell Culture & Counting.

Results

As apoptosis in transformed cells can be induced by glucose deprivation the ability of 2-MeOEMATE to inhibit glucose uptake was examined. Using MCF-7 cells uptake of deoxyglucose was shown to be linear with respect to cell number over the range 0.1–1.2×10$^6$ cells and over a 5–35 min period. Deoxyglucose uptake experiments were usually carried out with a 15min incubation period.

Figure 11A:
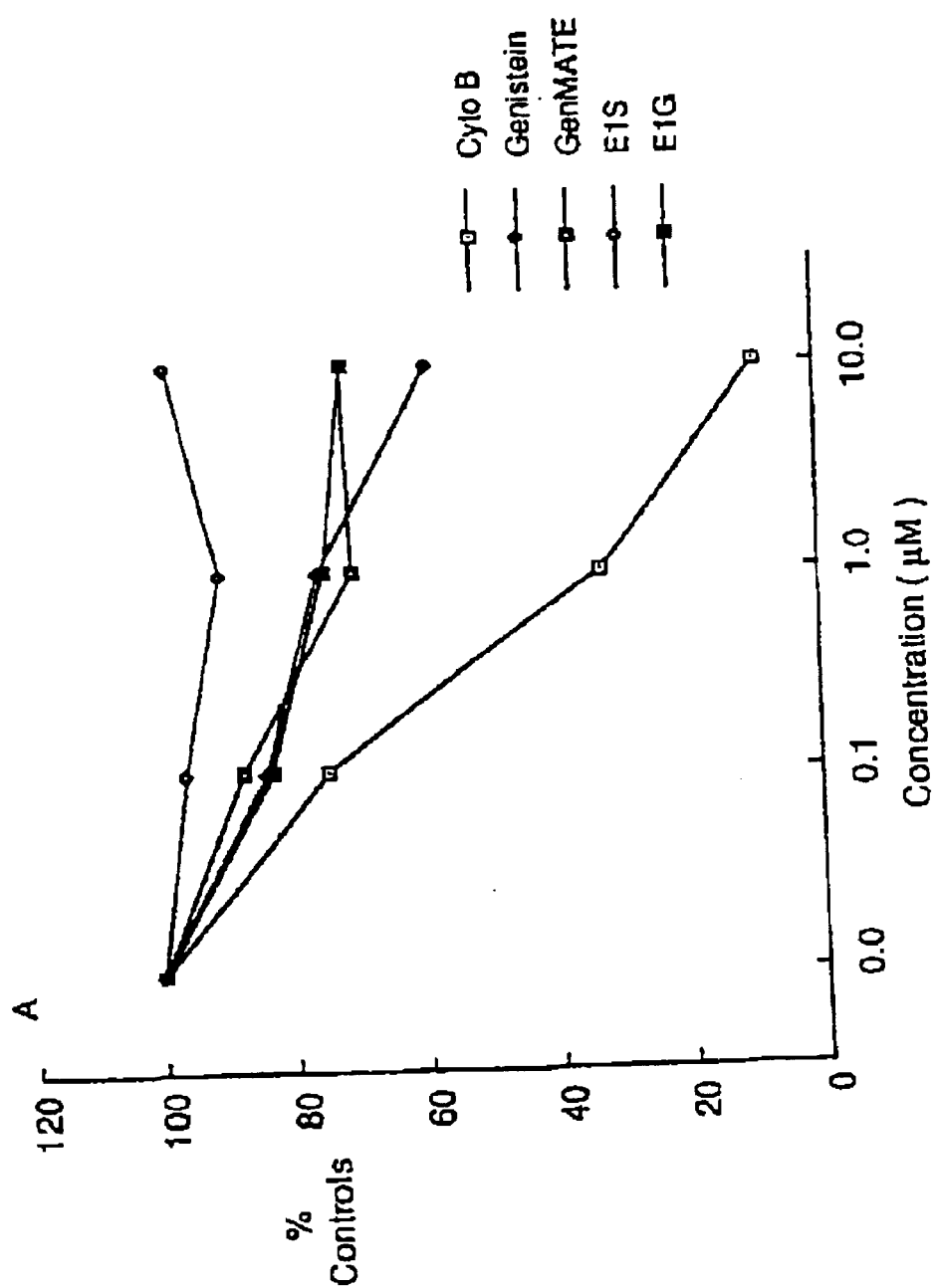
FIGS. 11A and 11B are graphs depicting inhibition of deoxyglucose uptake caused by known inhibitors of glucose uptake (11A) and estrogen conjugates (11B) as a function of the deoxyglucose uptake of controls.

The ability of two known inhibitors of glucose uptake, cytochalasin B and the isoflavone genistein, to inhibit uptake using this model was initially examined (22). Cytochalasin B (10 μM) inhibited deoxyglucose uptake by 91% while the effect of genistein, and its sulphamoylated derivative, at this concentration was lower (25%–42% inhibition) (FIG. 11a). At 100 μM genistein and its sulphamoylated derivative inhibited deoxyglucose uptake by 82% and 79% respectively (data not shown). An examination of the ability of two estrogen conjugates to inhibit uptake revealed that oestrone-3-sulphate was without effect whereas oestrone-3-glucuronide inhibited uptake by 29% (FIG. 11a).

Figure 11B:
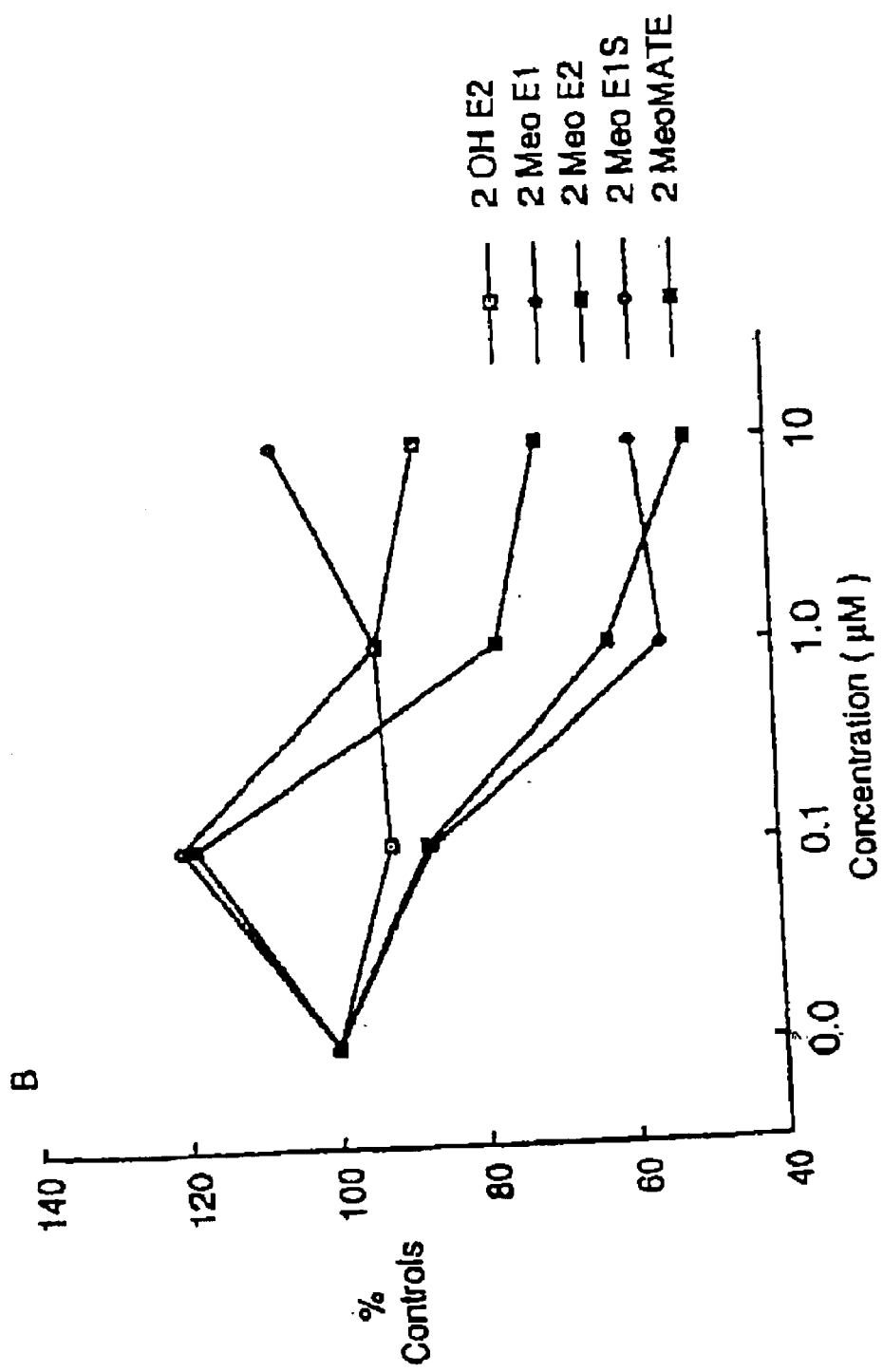

The effect of a number of estrogen metabolites on deoxyglucose uptake by MCF-7 cells is shown in FIG. 11b. 2-Hydroxyoestradiol, 2-MeOE2 or 2-MeOE1S had little effect on glucose uptake. In contrast, 2-MeOE1 and 2-MeOEMATE inhibited deoxyglucose uptake in a dose-dependent manner with 42% and 49% inhibition respectively occurring at 10 μM. While the extent of inhibition of deoxyglucose uptake resulting from exposure of cells to 2-MeOEMATE is similar to that observed for genistein. it is lower than that resulting from treatment of cells with cytochalasin B. 2-MeOEMATE (10 μM) also inhibited uptake of deoxyglucose in breast tumour-derived fibroblasts by 64% (data not shown).

Cell Culture & Counting

MCF-7 (estrogen receptor+ [ER+]) and MDA-MB-231 (ER−) breast cancer cells were obtained from the American Type Culture Collection (Rockville, Md.). Cells were routinely cultured in 25 cm$^2$ culture flasks in Eagle's minimum essential medium (EMEM) with Hepes buffer (20 mM). This medium was supplemented with L-glutarnine (2 mM), sodium hydrogen carbonate (10 mM), 1% non-essential amino acids and 5% (v/v) foetal calf serum (FCS). Before adding test compounds, cells were washed with phosphate-buffered saline (PBS) and treatments added in phenol-red free medium containing 2% stripped FCS and supplements. The effects of 2-MeOE1 or 2-MeOEMATE on the growth of MCF-7 cells was assessed using a Cell Titer 96 cell proliferation assay (Promega, Southampton, Hants, UK) according to the manufacturers' instructions. For this, cells (5000 per well) were cultured in medium containing phenol-red and 10% FCS and were exposed to a drug for 4 days before the assay was performed. For MDA-MB-231 cells. cell numbers were determined using a Coulter counter.

For the culture of fibroblasts, resected breast tumour tissue was minced and incubated in EMEM for 18–24h at 37° C. with collagenase (200 μg/ml). The dispersed cells were harvested by centrifugation and washed twice with medium to remove collagenase. Dispersed cells were seeded into culture flasks and grown to confluence before passaging on a weekly basis. For experimental purposes 12 well multi-well plates or 25 cm$^2$ flasks were seeded with fibroblasts and grown to 70–80% confluency. Cells were washed with PBS and exposed to drugs for 24h before determining cell numbers using a Coulter counter.

Photomicrographs of control and treated cells were taken under normal conditions of light and exposure using an Olympus SL35 Type 12 camera under an Olympus CK2 microscope (×100 magnification).

5. Tdt-mediated dUTP-nick end Labelling (TUNNEL) Analysis

The ability of 2-MeOEMATE to induce apoptosis in MCF-7 cells was examined by TUNEL analysis using an in situ cell death detection kit (Boehringer Manheim UK Ltd., Lewes, East Sussex, UK). Cells were fixed and permeabilised according to the manufacturers' instructions. Stained apoptotic cells were quantitated by flow cytometry.

Results

Figure 8:
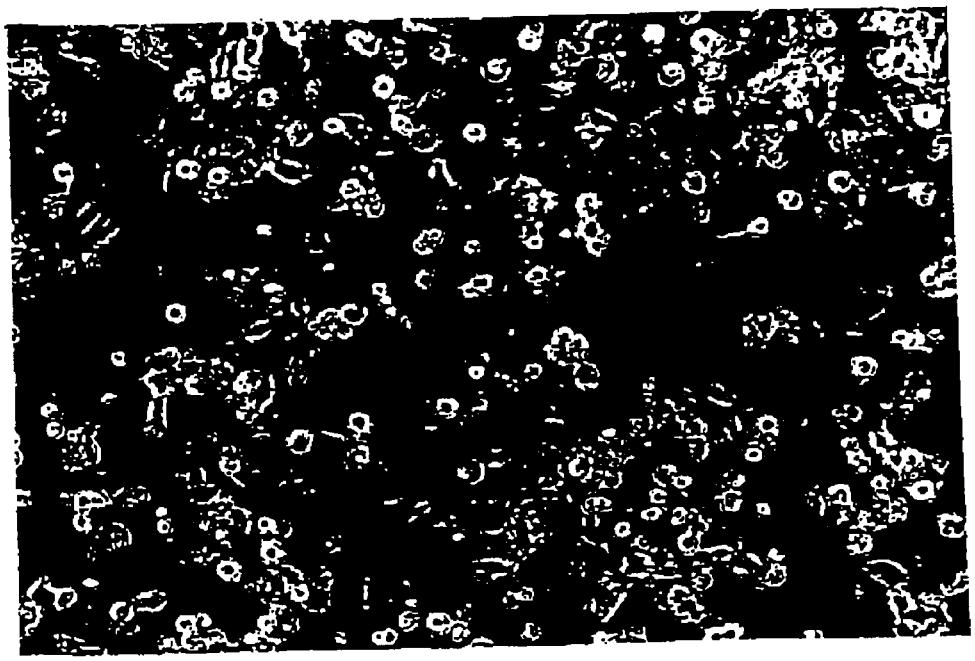

This possibility was confirmed in a further experiment by TUNEL analysis (FIG. 8). For untreated cells no increase in the proportion of fluorescently labelled cells was detected after staining. In contrast, there was a significant increase in the proportion of fluorescently labelled cells after exposure to 2-MeOEMATE (10 μM) for 48 h.

Fluorescently labelled cells represented approximately 10% of the cell population. This result indicates that 2-MeOEMATE can induce cells to undergo apoptosis.

Figure 12:
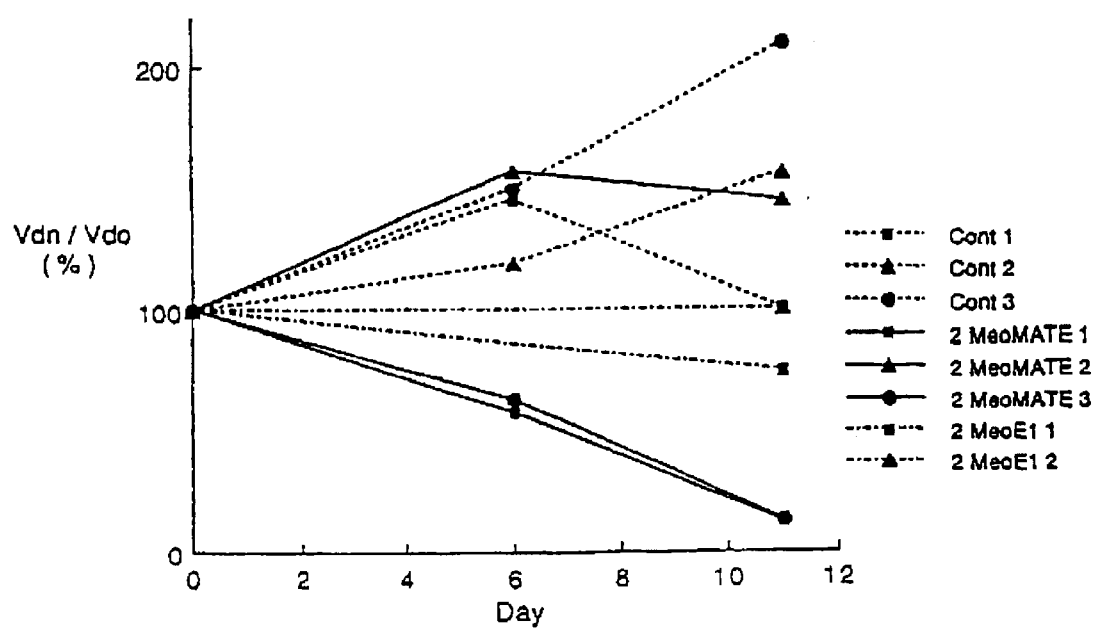
FIG. 12 is a graph depicting the effect of a control vehicle, 2-MeOEMATE and 2MeOE1 on tumor volume in vivo.

6. Effect of 2-MeOEMATE on Growth of NMU-induced Mammary Tumours in Intact Rats The effect of 2-MeOEMATE on mammary tumour growth was examined in a preliminary study using Ludwig rats (Harlan Olac, Bicester, UK) in which tumours were induced by inoculation of NMU. Tumour development was monitored regularly and when 0.5–1.0 cm³ in volume, animals received vehicle (propylene glycol, 200 μl/day, p.o.), 2-MeOEMATE (20mg/kg/day, p.o.) or 2-MeOE1 (20mg/kg/day, p.o.) daily for an 11 day period. Tumour length and width was measured with callipers and tumour volumes calculated as described (21).
Results A preliminary study was carried out to compare the abilities of 2-MeOE1 and 2-MeOEMATE to inhibit tumour growth in vivo. For this, the growth of mammary tumours was initiated by inoculation with NMU. Drugs were administered orally when tumour volumes reached 0.5–10 cm³. For two of the animals receiving vehicle, tumour volumes continued to increase (average 82%) while little change in the volume of a tumour in a third animal was detected (FIG. 12). For two animals receiving 2-MeOE1 no change in tumour volume occurred in one, while for the other a modest (25%) reduction was detected over the 11-day period of the study.

For three animals receiving 2-MeOEMATE the tumour volume in one animal continued to increase up to day 6, but thereafter showed a slight (8%) reduction. In contrast. for the two other animals receiving 2-MeOEMATE, tumours regressed rapidly and were barely palpable at the end of the 11-day period. Tumour volumes in the two animals receiving 2-MeOEMATE that regressed were monitored for a further 33 days during which time no regrowth of tumours was detected.

Hormono-ImmunoTherapy (H.I.T.)

Tumour necrosis factor a (TNFα) is a cytokine produced by macrophages, lymphocytes and other cells in the body. Recombinant TNFα has been used to treat a number of different types of cancer but so far has only met with limited success. In humans the severe side-effects induced by this cytokine have restricted its use for cancer therapy.

Our studies have revealed that a combination of an oxyhydrocarbyl steroidal sulphamate compound (in particular 2-methoxy EMATE/EMATE) with a biological reposnse modifier (in particular TNFα) may enhance the efficacy of this form of therapy.
A In vitro study Plates 1 and 2 have previously illustrated the effect of 2-methoxy EMATE (5 μM) on apoptosis induction in MCF-7 breast cancer cells (for details on these cells see PCT/GB92/01587). This study was extended to examine:

TABLE III

| Plate No. | % Apoptotic cells |
|---|---|
| Plate 7 MCF-7 cells + TNFα (10 ng/ml) | <1 |
| Plate 8 | >90 |

TABLE III-continued

| Plate No. | % Apoptotic cells |
|---|---|
| MCF-7 cells + 2-methoxy EMATE (1 μM) + TNFα (10 ng/ml) | |

Figure 9:
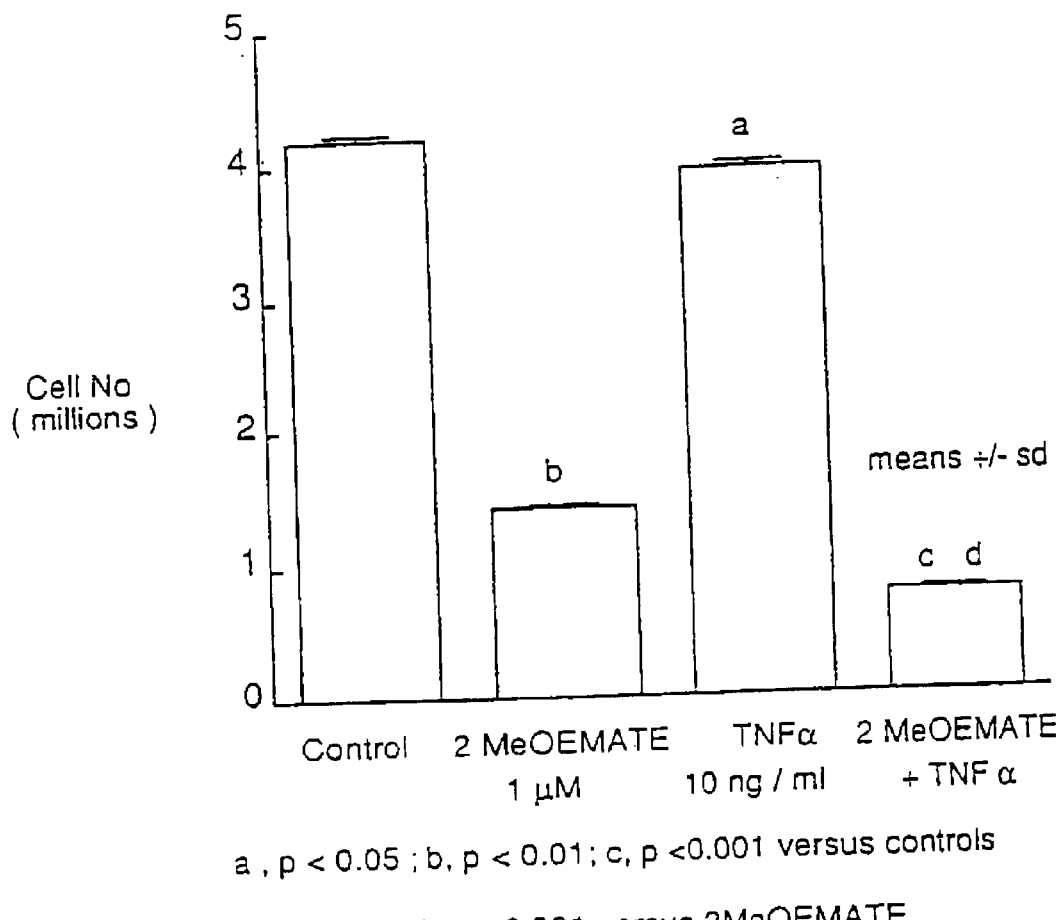
FIG. 9 is a bar chart depicting number of cells present in samples left untreated, treated with 2MeOEMATE, TNF$\alpha$, and 2 MeOEMATE and TNF$\alpha$.

In this experiment significantly less cells were present than in cells treated with only 2-methoxy EMATE. This finding was confirmed by counting the number of cells as shown in FIG. 9.

To assess the significance of this in vitro observation, an intact rat with an NMU-induced mammary tumour was treated with EMATE (20 mg/kg p.o.) for 3 days. It is generally known that oestrogens are metabolised via 2-hydroxylation with subsequent methylation. For days 2 and 3 in addition to EMATE, rat rTNFα (5 μg) was administered i.p. The dose appeared to be well tolerated.

Figure 10:
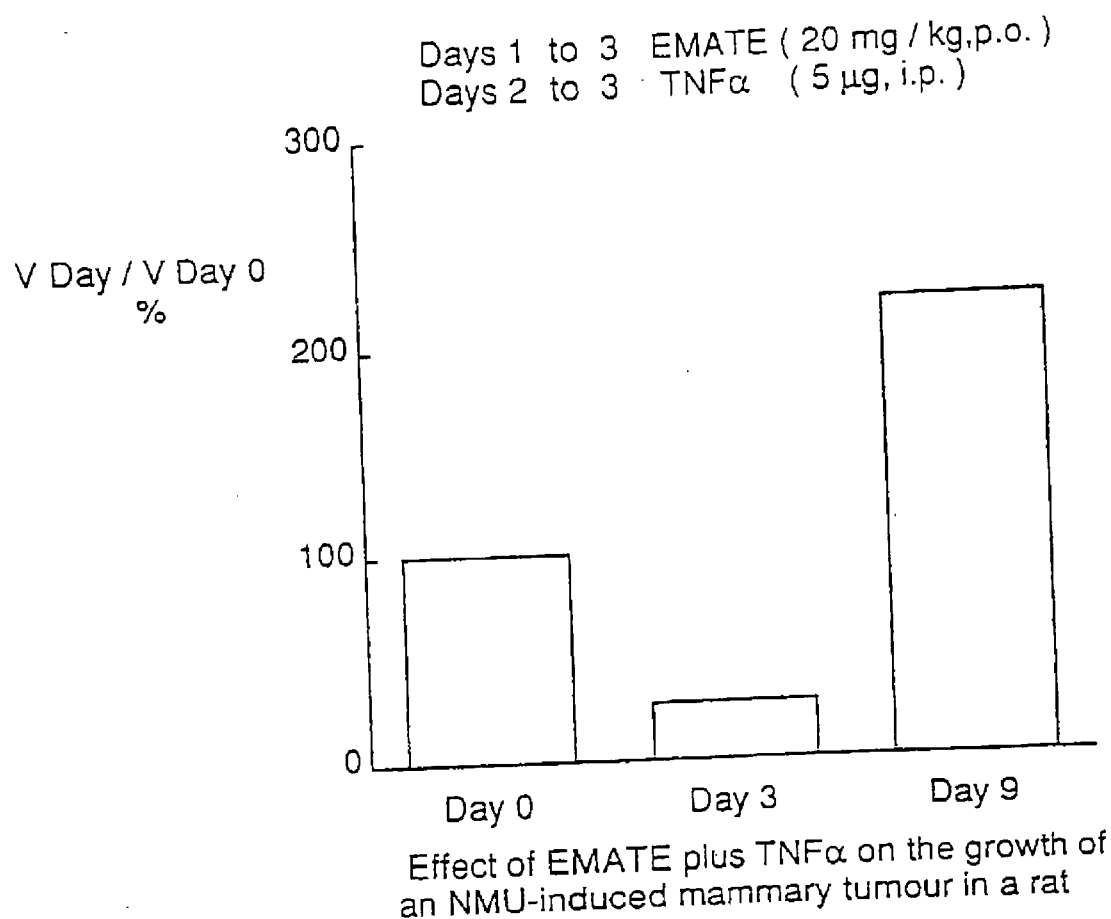
FIG. 10 is a bar chart depicting change in tumor volume as a function of the original tumor volume after treatment with EMATE from day 1 to 3 (20 mg/kg, p.o.) and TNF$\alpha$ from day 2 to 3 (5 $\mu$g, i.p.).

By day 3, the tumour volume had decreased by 72% compared with its volume before the start of treatment (FIG. 10). However, 6 days after the cessation of EMATE/TNFα therapy, the tumour had increased in volume by 120% compared with its Day 0 volume.

These results indicate that a combination of an oxyhydrocarbyl steroidal sulphamate compound and a steroidal sulphamate compound (in particular 2-methoxy EMATE/EMATE) plus a biological response modifier (in particular TNFα) may offer considerable therapeutic advantage for the treatment of tumours.

2 Methoxyoestrone

In this comparative example, two intact rats with NMU-induced mammary tumours were treated with 2 methoxyoestrone (20 mg/kg/d, p.o.) for 11 days. Tumour volumes were determined before (Day 0 volume) and at the end of the treatment with 2 methoxyoestrone (Day 11 volume).

The results are shown below:

TABLE IV

Effect of 2 methoxyoestrone on in vivo tumour growth

| | Vol $D_{11}$/Vol $D_0$ % |
|---|---|
| 1 | 75 |
| 2 | 100 |

These data highlight the surprising nature of the present invention.

DISCUSSION

Our findings show that it is possible to treat cancer with a combination of a sulphamate compound and a biological response modifier.

Our findings show that the combination of a sulphamate compound and a biological response modifier acts to inhibit cell-tumour growth by reducing glucose uptake by cancer cells and tumour-derived fibroblasts.

Our findings also indicate that the oxyhydrocarbyl steroidal sulphamate compound according to the present invention, especially 2-methoxy EMATE, acts to inhibit cell-tumour growth by reducing glucose uptake by cancer cells and tumour-derived fibroblasts. It is known that many cancers have an increased uptake of glucose and an increased rate of glucose metabolism. Transformation of cell lines results in the elevation of a protein that is involved in glucose uptake (glucose transporter, Glut 1). 3T3 Fibroblasts transfected with ras/src have an increased uptake of glucose (Flier et al., Science 235: 1492, 1987). Whereas glucose deprivation of normal rat fibroblasts did not induce apoptosis, glucose deprivation of c-myc transfected fibroblasts resulted in extensive apoptosis (Shim et al., Proc Natl Acad Sci, USE 95: 1511, 1998). Glut 1 is over expressed in breast tumours (Brown and Wahl, Cancer 72: 2979, 1993) but is not detectable in normal or benign breast tissues (Younes et al., Cancer Res. 56: 1164, 1996). Since cancer cells do not accumulate an intracellular store of glucose in the form of glycogen or fat, it must be obtained continuously from an external source and transported into the cell.

A key advantage of the present invention is that the composition of the present invention can also disrupt microtubules.

A key advantage of the present invention is that the oxyhydrocarbyl steroidal sulphamate compound according to the present invention, especially 2-methoxy EMATE, can also disrupt microtubules.

A key advantage of the present invention is that the composition of the present invention can induce apoptosis.

Another key advantage of the present invention is that the oxyhydrocarbyl steroidal sulphamate compound according to the present invention, especially 2-methoxy EMATE, can induce apoptosis. In this regard, while previous investigations have suggested that 2-methoxy E2 has potent antimitotic properties, results from our studies indicate that 2-methoxy EMATE inhibits cell growth by inducing apoptosis. Tumours grow if either the rate of cell growth (proliferation) is increased or rate of cell death (apoptosis) is decreased. In apoptosis, cells round up, sever connection with their neighbouring cells and DNA cleaves into oligonucleosomal fragments.

A further key advantage of the present invention is that the oxyhydrocarbyl steroidal sulphamate compound according to the present invention, especially 2-methoxy EMATE, can prevent and/or inhibit tumour angiogeneis.

A further key advantage of the present invention is that the composition of the present invention can prevent and/or inhibit tumour angiogeneis.

The present invention also provides compositions/compounds which:

1 cause inhibition of growth of oestrogen receptor positive (ER+) and ER negative (ER−) breast cancer cells in vitro by induction of apoptosis.

2 cause complete regression of ⅔rds of nitroso-methyl urea (NMU)-induced mammary tumours in intact (i.e. not ovariectomised) rats in 11 days.

3 inhibited the uptake of glucose in cancer cells, in particular in breast cancer cells and breast tumour-derived fibroblasts.

4 induce apoptosis, it is believed by disrupting microtubules (MTs), which form part of the cytoskeleton.

5. act in vivo by inhibiting angiogenesis.

Thus, in summary, the present invention provides a composition and compound suitable for use in the treatment of cancers and, especially, breast cancer.

In particular, in one aspect the present invention addresses the problem of blocking the growth of tumours in endocrine-dependent tissues (e.g. breast, endometrium, prostate). Nevertheless, other tumours (e.g. sarcomas, melanomas) should also be amenable to treatment with the composition and compound of the present invention.

It is also believed that the present invention has implications in treating hormonal conditions in addition to those associated with oestrogen. Hence, the present invention also provides a composition that is capable of affecting hormonal activity and is capable of affecting an immune response, wherein the composition is the composition of the present invention.

It is also to be understood that the composition of the present invention may have other important medical implications.

For example, the composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis. atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

All publications and patents mentioned in the above specification are herein incorporated by reference.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

What is claimed is:

1. A composition comprising
   i. a polycyclic sulphamate compound comprising a sulphamate group of the formula:

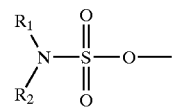

wherein each of $R_1$ and $R_2$ is independently selected from H or a hydrocarbyl group, or a pharmaceutically acceptable salt thereof and wherein the polycyclic sulphamate compound or pharmaceutically acceptable salt thereof inhibits steroid sulphatase and disrupts microtubules; and,
   ii. tumor necrosis factor alpha (TNF-α).

2. The composition of claim 1 wherein the steroid sulphatase is oestrone sulphatase.

3. The composition of claim 1 wherein if the sulphamate group on the polycyclic sulphamate compound were to be replaced with a sulphate group to form a sulphate compound then the sulphate compound would be hydrolosable by a steroid sulphatase enzyme (E.C.3.1.6.2).

4. The composition of claim 1 wherein if the sulphamate group on the sulphamate compound were to be replaced with a sulphate group to form a sulphate compound and incubated with a steroid sulphatase enzyme (E.C.3.1.6.2) at a pH of 7.4 and at 37° C. it would provide a $K_m$ value of less than 50 mM.

5. The composition of claim 1 wherein if the sulphamate group on the sulphamate compound were to be replaced with a sulphate group to form a sulphate compound and incubated with a steroid sulphatase enzyme (E.C.3.1.6.2) at a pH of 7.4 and at 37° C. it would provide a $K_m$ value of less than $\mu$M.

6. The composition of claim 1 where the composition further comprises a pharmaceutically acceptable carrier, diluent, or excipient.

7. The composition of claim 1 wherein the polycyclic sulphamate compound is a steroid sulphamate.

8. The composition of claim 7 wherein the sulphamate group is attached to the 3 position of the A ring of the steroidal nucleus.

9. The composition of claim 7 wherein the steroid sulphamate is oestrone-3-sulphamate.

10. The composition of claim 1 wherein the steroid suiphamate comprises at least one oxyhydrocarbyl group.

11. The composition of claim 10 wherein the oxyhydrocarbyl group is attached to the position of the A ring of the steroidal nucleus.

12. The composition of claim 11 wherein the oxyhydrocarbyl has the formula $C_{1-6}O$.

13. The composition of claim 1 wherein the polycyclic sulphamate compound is an oxyhydrocarbyl steroid sulphamate compound or a pharmaceutically active salt thereof.

14. The composition of claim 13 wherein the oxyhydrocarbyl steroid sulphamate is 2-methoxyoestrone-3-O-sulphamate.

* * * * *